United States Patent [19]

Lue et al.

[11] Patent Number: 4,982,731
[45] Date of Patent: Jan. 8, 1991

[54] IMPLANTABLE SYSTEM AND METHOD FOR AUGMENTING PENILE ERECTION

[75] Inventors: Tom F. Lue, Millbrae; Emil E. Tanagho; Richard A. Schmidt, both of San Rafael; Curtis A. Gleason, Palo Alto, all of Calif.

[73] Assignee: The Regents of the University of California, Oakland, Calif.

[21] Appl. No.: 262,890

[22] Filed: Oct. 26, 1988

[51] Int. Cl.$^5$ .............................................. A61F 2/26
[52] U.S. Cl. ................................................... 128/79
[58] Field of Search ................. 128/79, 327, DIG. 25, 128/346

[56] References Cited

U.S. PATENT DOCUMENTS

| | | | |
|---|---|---|---|
| 2,455,859 | 12/1948 | Foley | 128/79 |
| 4,408,597 | 10/1983 | Tenney, Jr. | 128/DIG. 25 |
| 4,428,365 | 1/1984 | Hakky | 128/DIG. 25 |
| 4,523,584 | 6/1985 | Yachia et al. | 128/79 |
| 4,585,005 | 4/1986 | Lue et al. | 128/419 R |
| 4,602,625 | 7/1986 | Yachia et al. | 128/79 |
| 4,660,558 | 4/1987 | Kees, Jr. | 128/346 |
| 4,723,538 | 2/1988 | Stewart et al. | 128/79 |
| 4,829,990 | 5/1989 | Thuroff et al. | 128/79 |

OTHER PUBLICATIONS

Lue et al., "Early Recognition and Management of Impotent Patients," *Family Medicine*, vol. 1, No. 10–11/7/83, pp. 59–64.
Lue, "Evaluation and Treatment of Impotence—Where are we Going/48 ," *West, J. Med.*, 4/85, 142:546.
Lue et al., "Vasculogenic Impotence Evaluated by High-Resolution Ultrasonography and Pulsed Doppler Spectrum Analysis," *Radiology*, 1985, pp. 777–781.

*Primary Examiner*—Cary E. Stone
*Attorney, Agent, or Firm*—Phillips, Moore, Lempio & Finley

[57] ABSTRACT

A method and system for augmenting penile erection in a human male is disclosed. An inflatable cuff is placed circumferentially around the corpora carvernosa, the deep dorsal vein, and the cavernous veins, adjacent to the hilum of the penis. Selective compression of the cuff will function to restrict venous drainage to augment penile erection. The cuff is adapted to have opposite ends thereof attached together and at least one inflatable vesicle is formed on the inner side of the cuff. A pump, including an attandant control system, is sized for implantation in a scrotum whereby the pump can be selectively squeezed to inflate and fluid pressurize the vesicle to compress the cuff around the penis. A control circuit, connected between the cuff and the pump, functions to automatically deflate the cuff after a predetermined period of time has elapsed.

19 Claims, 7 Drawing Sheets

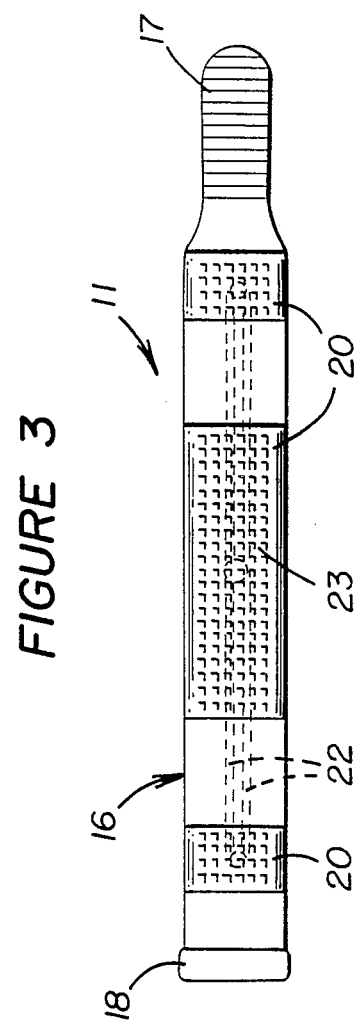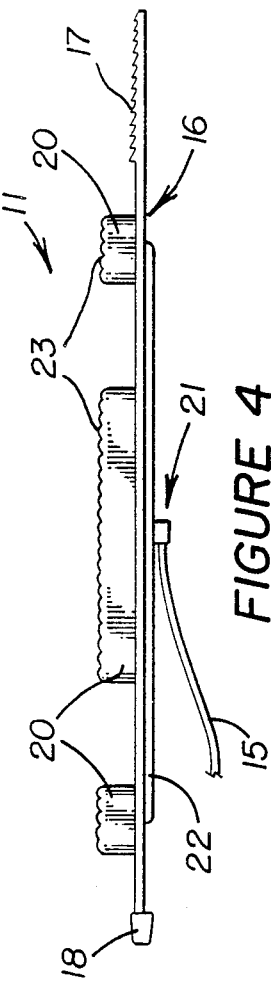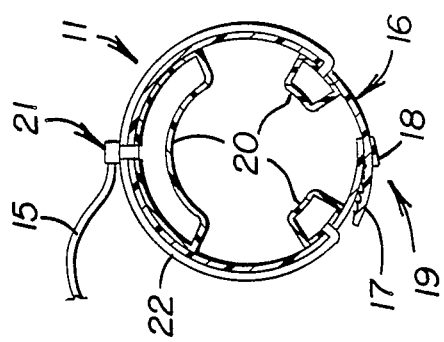

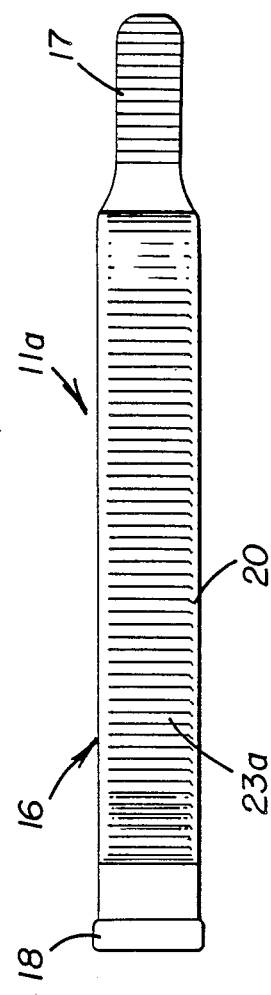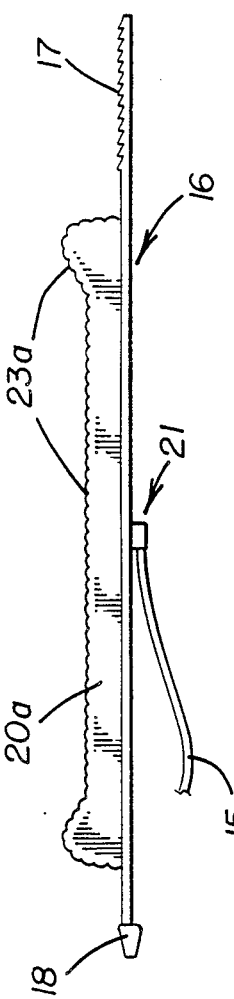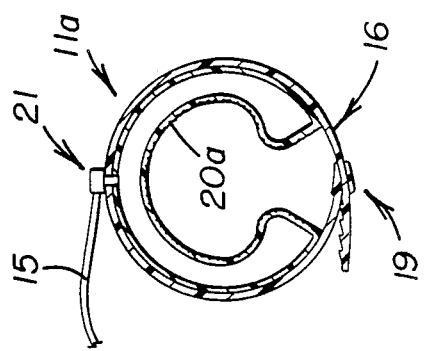

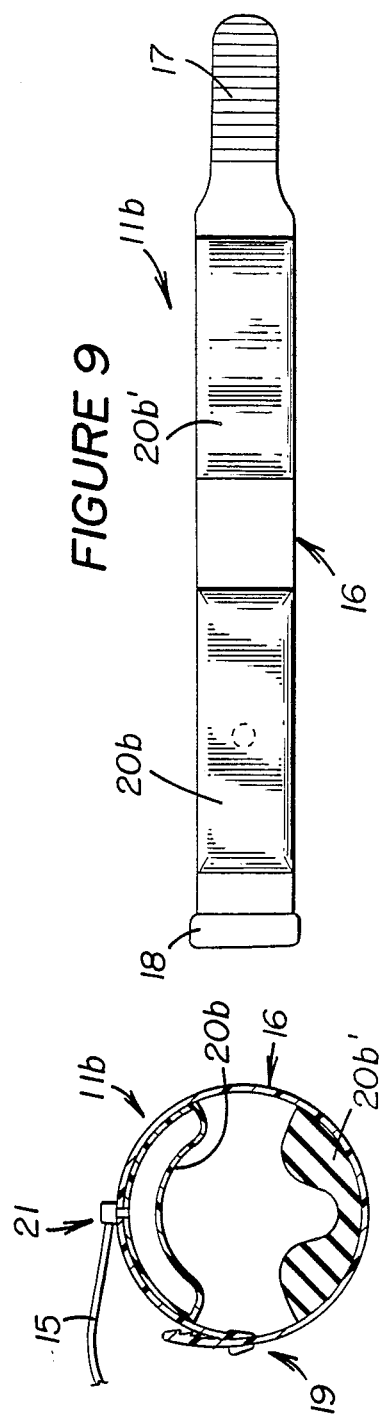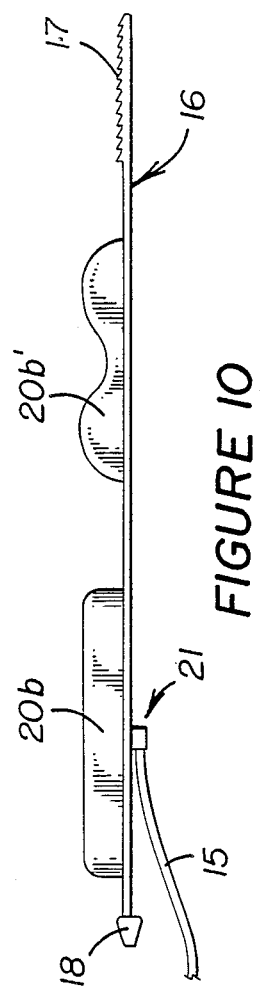

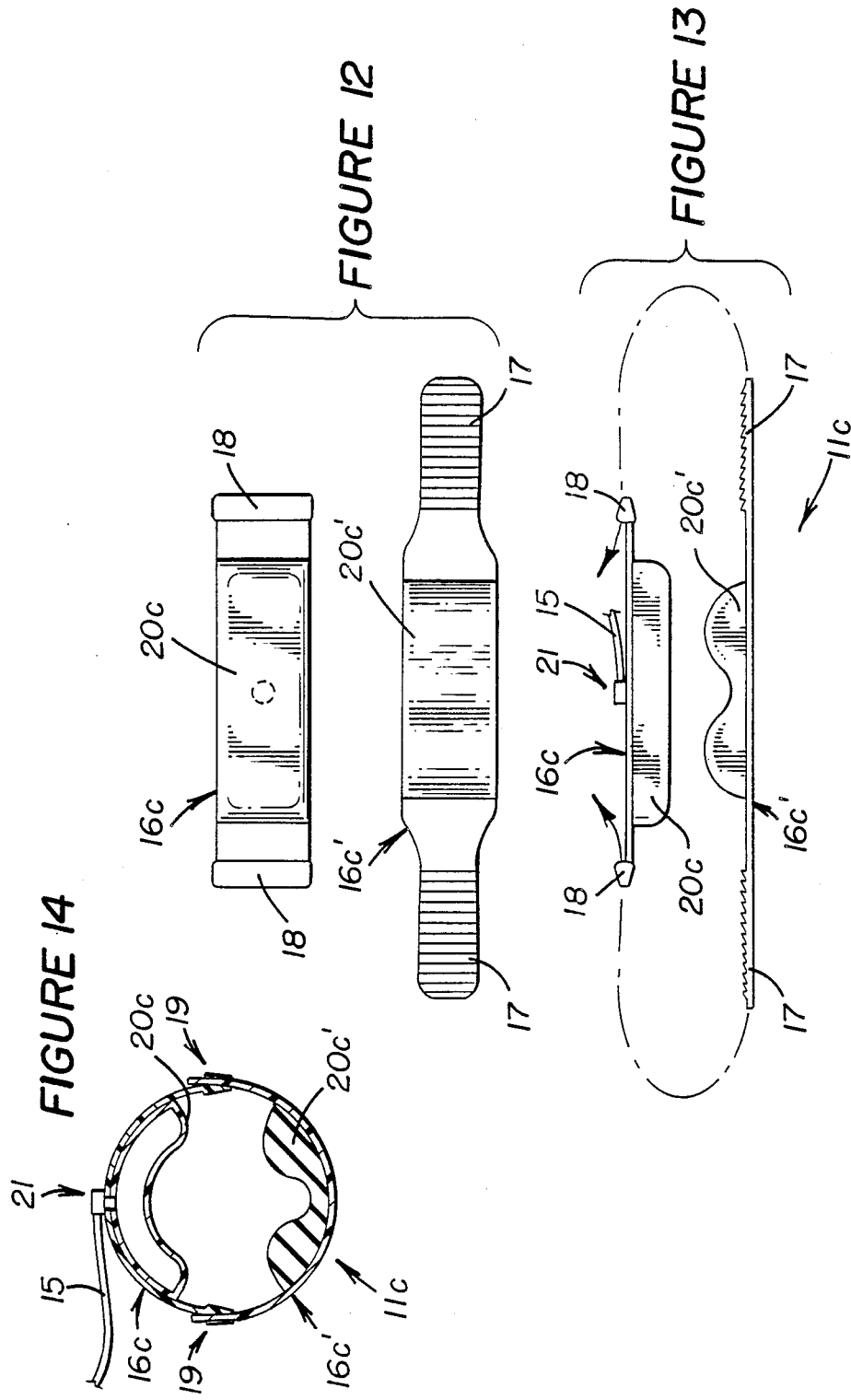

IMPLANTABLE SYSTEM AND METHOD FOR AUGMENTING PENILE ERECTION

ACKNOWLEDGEMENT

This invention was made with partial Government support under grant No. HD-19640 awarded by the Department of Health and Human Services. The Government has certain rights in this invention.

TECHNICAL FIELD

This invention relates generally to a system and method for augmenting penile erection and more particularly to an implantable penile erection control system for patients who are incapable of obtaining and maintaining a firm erection spontaneously.

BACKGROUND OF THE INVENTION

The ability to achieve and sustain penile erection is a basic requirement for a male to have children and a happy marriage. The need to provide a controlled and sustained penile erection in impotent patients is well documented. Impotency may be due to a variety of causes, such as drugs, systemic disease, psychological, neurological, hormonal, arterial, venous or cavernous smooth muscle disorders. It has been estimated that more than ten million American males are impotent.

Along with the work of other researchers, applicants' extensive research on the anatomy, physiology, neuroanatomy, hemodynamics, pharmacology, radiology and ultrastructure of the penis has already revolutionized the diagnosis and treatment of impotence. For example, applicants' U.S. Pat. No. 4,585,005 discloses a system and method for augmenting penile erection electronically.

Hemodynamically, applicants' studies have shown that penile erection is a result of increased arterial blood flow, increased venous resistance and relaxation of the sinusoids within the corpora cavernosa. The vascular smooth muscle surrounding the sinusoids and the arteriolar wall is a primary consideration for controlling these events. In the flaccid state, the tonic discharge of the sympathetic nervous system maintains the muscles in a contracted state which allows minimal arterial flow into the penis.

Neurotransmittors (possibly a combination of acetylcholine, endothelial derived relaxing factor, vasoactive intestinal polypeptide and inhibition of alpha adrenergic tone) released as a result of sexual stimulation relaxes the vascular smooth muscles and results in large influx of arterial flow, expansion of the sinusoids and tumescence of the penis. Expansion of the sinusoids within a relatively confined space, limited by the tunica albuginea, compresses the subtunical draining venous channels which lie between the sinusoidal wall and the tunica albuginea before exiting as emissory veins. The nearly total closure of the draining venous system effectively contains most of the incoming blood within the sinusoids and results in engorgement, elongation and rigidity of the penis.

Applicants' studies have further shown that among the causes of erectile impotence, the final common pathway is the inability to initiate, store and maintain blood within the corpora cavernosa In non-vascular impotence, although the arterial, muscular and venous systems are intact, psychologic factors, nerve dysfunction or hormonal imbalance will result in a lack of neurotransmittors and inadequate erection In vascular impotence, most patients are still capable of realizing partial erection, but are unable to achieve coitus due to partial rigidity or inability to maintain the erection.

A more accurate diagnosis of various types of impotence are now possible due to the recent introduction of several innovative diagnostic tests The addition of rigiscan to nocturnal penile tumescence testing allows better assessment of penile rigidity during sleep and thus more accurate differentiation of psychogenic from organic impotence. The use of intracavernous injection of vasodilators, such as papaverine or prostaglandin E-1, allows office observation of a patient's erectile capability. When ultrasound and pulsed Doppler wave analysis is performed, before and after vasodilator injection, accurate functional evaluation of the penile arteries can be made. Pharmacologic cavernosometry and cavernosography can further assess the degree and location of venous incompetence. Several techniques of nerve conducting tests have also been developed for the evaluation of penile nerves and neurogenic impotence.

The treatment of erectile impotence has largely depended on sex therapy or psychotherapy, before the advent of implantable penile prosthesis. Various types of implantable prosthesis provide an effective tool for restoring the ability to achieve and maintain penile erection. However, the insertion of a foreign substance, whether of the inflatable or semirigid prosthesis type, invariably incites a scarring reaction and normally destroys substantial amounts of penile erectile tissues.

The recent introduction of intracavernous injection of pharmacologic agents, such as papaverine, papaverine with phentolamine, or prostaglandin E-1, has received wide attention. In non-vascular or minimal vasoular impotent patients, injection of these vasoactive substances induces erection, lasting for a variable period of time, e.g., from several minutes to several hours Two major complications have been observed priapism and fibrosis of the corpora cavernosa. If not promptly treated, priapism will result in extensive necrosis of the penile tissues and complete fibrosis of the corpora cavernosa. Long term injection of the papaverine can also induce extensive scarring of the penile erectile tissue.

Another modality that has been introduced recently is the vacuum suction device for penile erection The penis is placed within a suction device for several minutes until tumescence occurs. A tourniquet is then applied tightly and exteriorly at the base of the penis to restrict all venous outflow. The major disadvantage of this device is numbness and petechia of the penile skin after several minutes of tight proximal constriction.

None of the above systems or methods is ideal for all classes of impotent patients.

SUMMARY OF THE INVENTION

An object to this invention is to provide an improved implantable system and method for augmenting penile erection that overcomes the above briefly described problems and deficiencies of the prior art. In particular, the system and method of this invention will achieve prolonged rigidity of a penis without destroying penile erectile tissue and/or cause numbness or petechiae of the penile skin. The system can be used in the same groups of patients that heretofore used penile protheses, such as those suffering from severe vascular insufficiency, intractable psychogenic impotence or the like. The system can be used for those patients who are incapable or reluctant to accept penile injection therapy.

Further, the system can be used to enhance and maintain the erection induced by vacuum suction or injection.

The method for augmenting penile erection in a human male first comprises: Identifying the corpora cavernosa, corpus spongiosum, tunica albuginea corporum cavernosorum, dorsal artery, dorsal nerve, cavernous veins, and deep dorsal vein adjacent to the hilum and root of a penis; placing compression means at least around the corpora cavernosa, cavernous veins, and deep dorsal vein, adjacent to the hilum, outside the tunica albuginea corporum cavernosorum, and under the dorsal artery and dorsal nerve; selectively compressing the compression means to apply pressure against the corpora cavernosa, cavernous veins, and deep dorsal vein to restrict venous flow of blood therethrough and to enhance erection of the penis for a predetermined time period; and removing the applied pressure after such time period has elapsed.

In the preferred system embodiment of this invention, the compression means comprises a cuff composed of a biocompatible material and having a length substantially the same as the circumference of a penis. Connector means releasably attach opposite ends of the cuff together and at least one inflatable vesicle is positioned on an inner side of the cuff. Pump means, sized for implantation in a scrotum, is adapted to selectively inflate the vesicle to compress the cuff around the penis when the cuff is attached therearound. The pump means includes a reservoir and control means for automatically deflating the cuff.

BRIEF DESCRIPTION OF THE DRAWINGS

Other objects and advantages of this invention will become apparent from the following description of the accompanying drawings wherein:

FIG. 3 is a top plan view of the inside of the cuff in its flattened condition;

FIG. 4 is a side elevational view of the cuff;

FIG. 5 is an end elevational view of the cuff in its closed position, as further shown in FIG. 1;

FIGS. 6-8 are views similar to FIGS. 3-5, respectively, but illustrate a first modification of the cuff;

FIGS. 9-11 are views similar to FIGS. 3-5, respectively, but illustrate a second modification of the cuff;

FIGS. 12-14 are views similar to FIGS. 3-5, respectively, but illustrate a fourth modification of the cuff;

DESCRIPTION OF THE PREFERRED EMBODIMENTS

Definition of Terms

Figure 1:
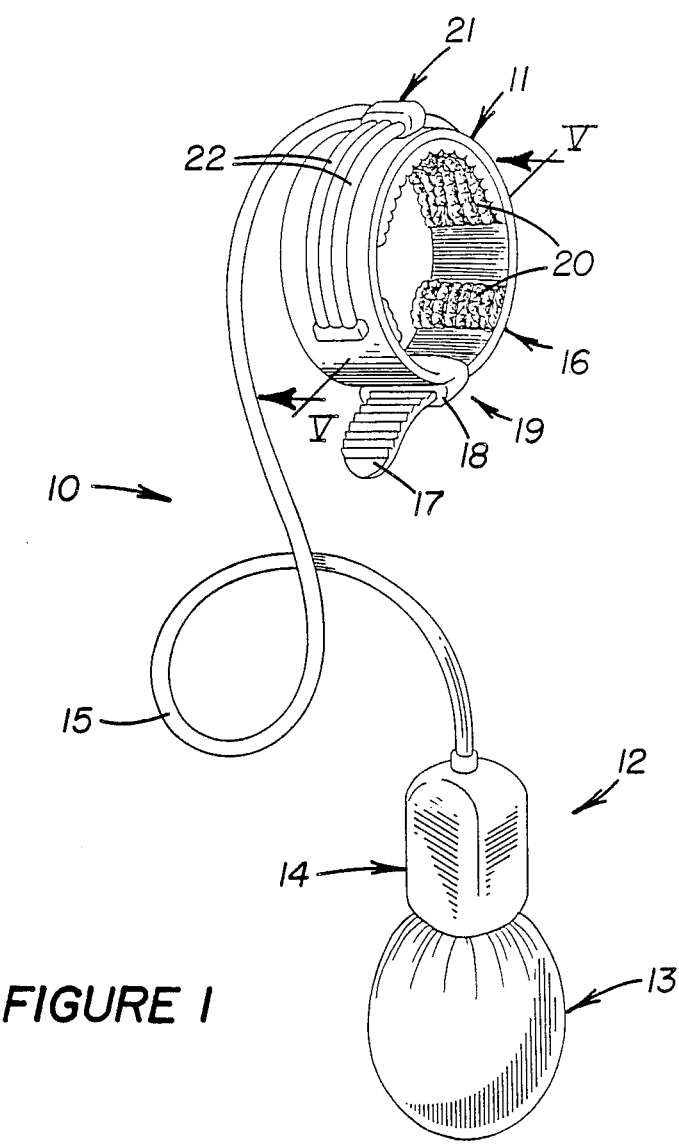
FIG. 1 is an isometric view illustrating an implantable system for augmenting penile erection, including an inflatable cuff adapted to be attached around a penis and a pump adapted for implantation in a scrotum for selectively inflating the cuff.

The following terms and definitions are used herein for the sake of clarity and understanding of this invention. Although some of the terms have broader meanings, the terms are used in the context of the invention disclosed and claimed herein. The capital letters (A through I) accompanying some of the terms correspond to those set forth in the specification an shown in the drawings.

Cavernous veins (J): Veins that return the blood from the proximal portion of the corpora cavernosa to the deep dorsal vein of the penis or the internal pudendal vein.

Caverns: Cavities, such as caverns of corpora cavernosa or corpus spongiosum that form dilatable spaces that fill with blood and become distended with erection of the penis.

Corpus: Discrete masses of material, as of specialized tissue; used in anatomical nomenclature to designate the entire organism, and applied also to a main portion of an anatomical part, structure, or organ.

Corpora cavernosa (B): Cavernous body of the penis comprising a pair of generally cylindrical and side-by-side columns of erectile tissue forming the dorsum and sides of the penis. Commonly called the spongy body of penis.

Corpus Spongiosum (C): Generally cylindrical body or column of the penis positioned in a groove defined on the underside of the corpora cavernosa. The urethra passes through the corpus spongiosum.

Dorsal artery (E): One of the arteries of the penis that originates at the internal pudendal artery and terminates at the glans of penis.

Dorsal nerve (F): Deepest division of the internal pudendal nerve that parallels the dorsal artery in the body of the penis.

Deep Dorsal vein (G): Deep vein of the penis that lies subfascially in the midline of the penis adjacent to the dorsal arteries.

Hilum (H): The depression or pit at the root of the penis whereat the vessels and nerves enter.

Internal pudendal artery: Artery that connects to the dorsal artery and ends its origin at the internal iliac artery.

Penis: The male organ of copulation and of urinary excretion, comprising a root, body, and extremity, or glans penis. The root is attached to the descending portions of the public bone by the crura, the latter being the extremities of the corpora cavernosa. The body consists of the parallel corpora cavernosa and corpus spongiosum.

Scrotum (A): The pouch that contains the testes and their accessory organs.

Suspensory ligament: Band of fibrous tissue attaching the root of the penis to the front of the symphysis pubis. The suspensory ligament splits into two portions at its connection with the root of the penis and blends with the fascial sheath thereof.

Tunica albuginea corporum cavernosorum: The fibroelastic sheath that encloses the corpora cavernosa.

Tunica albuginea corporis spongiosi: The fibroelastic sheath that encloses the corpus spongiosum of the penis.

Urethra (I): The membranous canal, extending through the corpus spongiosum, conveying urine from the bladder to the exterior of the penis. The urethra also form a duct for conveying seminal fluid therethrough.

GENERAL DESCRIPTION

Penile erection involves arterial dilation with increased flow of blood to the penis, relaxation of the smooth muscles within the penis and compression of the penile veins to reduce venous drainage. Applicants' clinical studies of over 1,200 patients with ultrasound and pulsed Doppler analysis, before and after intracavernous injection of papaverine, revealed that more than 75% of the patients tested had some degree of arterial insufficiency or venous incompetency resulting in their inability to achieve and maintain penile erection.

Figure 2:
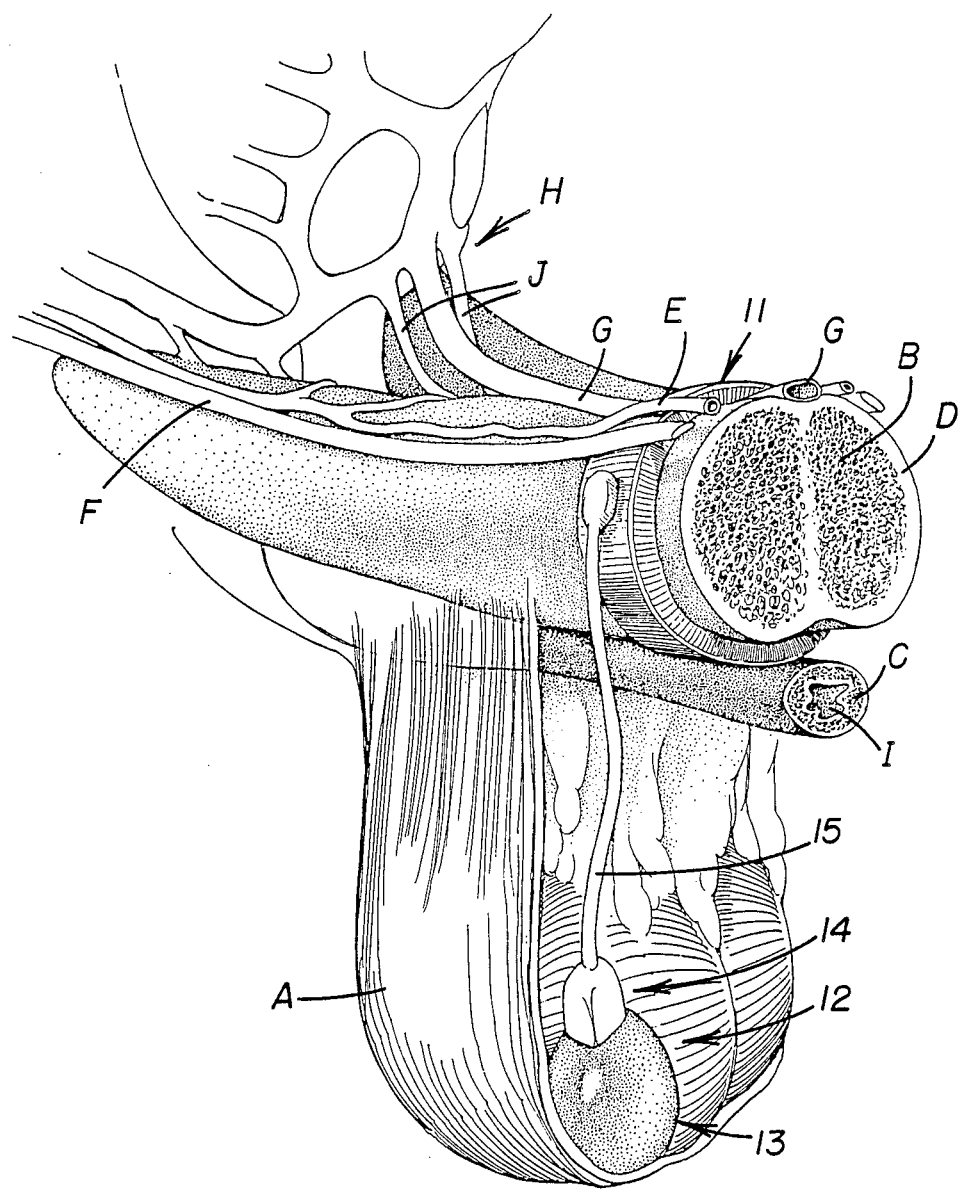
FIG. 2 illustrates implantation of the system on the penis of a patient.

Referring to FIGS. 1 and 2, an augmenting system or device 10 is adapted to be implanted in a human male to selectively enhance penile erection. The system essentially comprises an inflatable cuff 11, adapted to be formed into an annular band releasably attached around a penis, and pump means 12. The pump means includes a squeezable pump and combined reservoir 13 and an inflation and deflation control system or circuit 14, connected to the cuff by a primary tube 15. The reservoir of the pump contains a volume of working fluid (e.g., 10 ml), such as saline or other suitable liquid.

As further shown in FIG. 2, the system is surgically implanted in a patient so that cuff 1; circumvents critical areas of the penis and pump means 12 is disposed in a scrotum A. The patient is thus enabled to enhance erection by finger-depressing and releasing pump 13 an appropriate number of times to restrict venous drainage, as described more fully hereinafter. The cuff deflates automatically, after the desired erectile time period has been achieved.

METHOD FOR AUGMENTING PENILE ERECTION

Referring the FIGS. 2, the preferred method for augmenting penile erection in a human male first comprises identifying those portions of the suspensory ligaments, corpora cavernosa B, corpus spongiosum C, tunica albuginea corporum cavernosorum D, dorsal artery E, dorsal nerve F, cavernous veins J, and dorsal vein G, that are adjacent to hilum H and the root of the partially illustrated penis. FIG. 2 illustrates placing cuff or compression means 11 around corpora cavernosa B, cavernous veins J, and deep dorsal vein G, adjacent to hilum H and outside the tunica albuginea corporum cavernosorum D of the corpora cavernosa. The cuff is further placed under dorsal artery E and dorsal nerve F and proximal to the suspensory ligaments (not shown). The latter positioning will insure a normal penile erection, i.e., in a normal upward direction.

Alternatively and for patients complaining of inadequate engorgement of glans, the cuff can be placed around both corpora cavernosa B and corpus spongiosum C whereby upon inflation of the cuff, all blood from the penis will be temporarily restricted and maximal engorgement of glans will be obtained in addition to enhanced erection and rigidity of the corpora cavernosa.

Thus, the above surgical procedures can be contrasted with conventional surgical procedures wherein a prothesis device is inserted directly within a corpora cavernosa. As described above, the latter procedures induce a scarring reaction and destruction of penile erectile tissue. The critical placement of cuff 11 on the penis prevents the same.

In carrying forth the surgical procedure illustrated in FIG. 2, proper dissection steps, now obvious to those skilled in the art, are accomplished to prevent paresthesia or pain from the compression of dorsal nerve F and to permit ejaculation. In the case of the above-described alternative surgical procedure wherein the cuff is placed around both corpora cavernosa B and corpus spongiosum C, the patient is unable to ejaculate due to compression of urethra I. After the healing process has occurred, the patient is then enabled to selectively finger-squeeze and compress pump 13 a sufficient number of times to inflate cuff 11 to restrict venous drainage from the dorsal vein and corpora cavernosa to augment erection. Overinflation is prevented, as described more fully hereinafter.

DESCRIPTION OF AUGMENTING SYSTEM 10

Referring to FIGS. 1 and 3–5, the various components of augmenting system 10 may be composed of any suitable medical grade and bio-compatible plastic material suitable for purposes described herein. For example, cuff 11 and pump 13 may be composed of a standard polyurethane material marketed under the trademark Bioflex. Polyurethane materials of this type have been found to exhibit the durability required for application of this invention.

Alternatively, the material may constitute medical grade Silastic which is a composition in physical character comparable to milled and compounded rubber prior to vulcanization, but containing organosilicon polymers. Components fabricated from this material are serviceable from $-73°$ to $+160°$ C., retain good physical and dielectric properties when placed in a patient, and exhibit excellent resistance to compression set, weathering, and corona. In addition, thermal conductivity of this material is high and water absorption is low.

As shown in FIG. 3, when cuff 11 is in its flattened condition, it forms a strap 16 having a serrated tongue 17 formed on one end and a socket 18 formed on the other end thereof to form a standard snap-in connector 19 (FIG. 5) when the tongue is inserted into the flexible socket. The circumferential length of the cuff, substantially the same as the circumference of a particular penis, is thus made adjustable with tongue 17 being closely fitted within socket 18 to normally hold them in a locked condition, relative to each other, when placed as a band around a penis (FIG. 2).

In the embodiment illustratrated in FIGS. 1 and 3–5, three longitudinally spaced and co-planar vesicles 20 (FIG. 3) are formed integrally on the inner side of strap 16 to each define an inflatable chamber therein. Primary tube 15 communicates with the intermediate vesicle via a connection 21 and with the two outer vesicles via the connection and secondary tubes 22. As shown in FIG. 5, when the cuff is formed into an annular band, the intermediate vesicle is at least generally diametrically opposed to the two outer vesicles.

The size and arrangement of a vesicle or vesicles are pre-selected in all described embodiments to apply compressive pressure at selected areas of corpora cavernosa B, cavernous veins J, and dorsal vein G (FIG. 2) and also corpus spongiosum C if the above-described alternative surgical procedure is followed.

Inner surfaces 23 of the vesicles (as well as other vesicles described hereinafter) may be channeled or otherwise textured to aid in remaining the cuff in its proper position on the penis and to aid in the compressive desiderata herein described.

FIGS. 6–8 illustrate a modified cuff 11A wherein identical numerals depict corresponding constructions, but with modified constructions appearing in the figures being accompanied by an "a." In this embodiment of the invention, a single vesicle 20a is integrally formed on the inner surface of strap 16, substantially throughout its length, to have its single inflatable chamber communicate with primary tube 15 via connection 21 As shown in FIG. 7, the opposite ends of vesicle 20a define raised end portions and an immediate planar portion, in contrast to the FIG. 4 embodiment wherein the inner surfaces of vesicles 20 are generally co-planar.

FIGS. 9-11 illustrate a modified cuff 11b wherein a pair of longitudinally spaced vesicles 20b and 20b' are longitudinally spaced relative to each other whereby they become diametrically opposed when the cuff assumes its annular band or circular configuration, circumferencially about a penis (FIG. 11). In this embodiment, vesicle 20b is inflatable, via tube 15, whereas vesicle 20b' is not and may be formed of a suitable solid medical grade elastomer, such as a suitably compounded polyurethane material. In this embodiment an inner surface of vesicle 20b is generally planar whereas an inner surface of vesicle 20b' is generally smooth and defines a concavity therein.

FIGS. 12-14 illustrate a modified cuff 11c having a two-part strap attached together by a pair of diametrically opposed connectors 19 (FIG. 14). As shown in FIGS. 12 and 13, a first strap portion 16c has an inflatable vesicle 20c formed integrally on an inner surface thereof with a socket 18 being formed at each end of the strap portion. Primary tube 15 communicates with the inflatable chamber of vesicle 20c via connection 21. A second strap portion 16c' has a serrated tongue 17 formed on each end thereof and a solid non-inflatable elastomeric pad 20c' formed integrally on an inner surface thereof.

Pump 13 is preferably in the form of an elastomeric bulb or bladder that is sized, along with its attendant control system 14, to fit within scrotum A without damaging the testes. The bulb is sufficiently flexible and exhibits appropriate physical properties to enable it to be squeezed and released to assume its normal expanded condition for reception of the working fluid.

Figure 15:
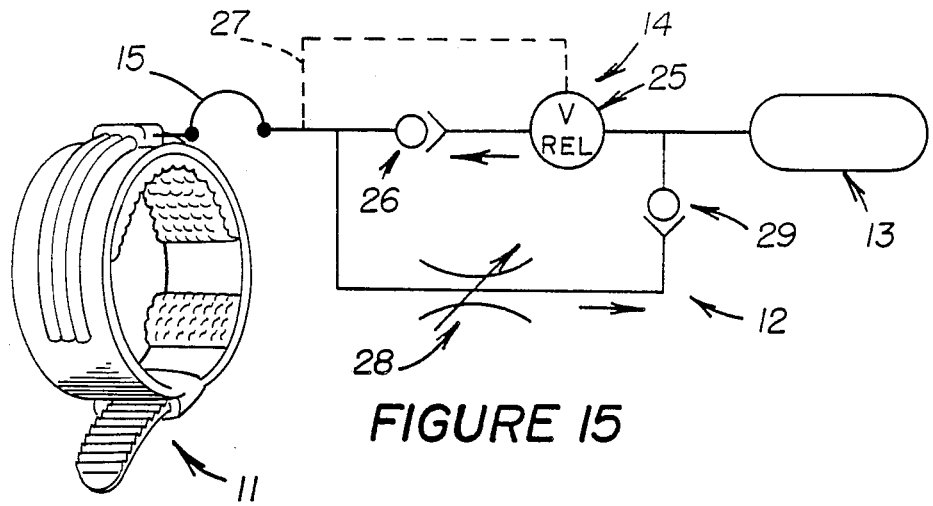
FIG. 15 schematically illustrates a control circuit, including the pump, for selectively inflating the cuff of FIG. 1.

Referring to FIG. 15, combined pump and reservoir 13 is adapted to charge fluid, such as saline or other suitable liquid, to cuff 11 via a relief valve 25, a one-way check valve 26 and primary tube 15. A conduit 27, formed within control circuit 14, will relieve fluid pressure prevalent in the chamber of a particular vesicle, when such pressure exceeds a preset maximum, to prevent penile damage. A metered flow restrictor 28 connects primary tube 15 to pump/reservoir 13 via a one-way check valve 29.

Figure 16:
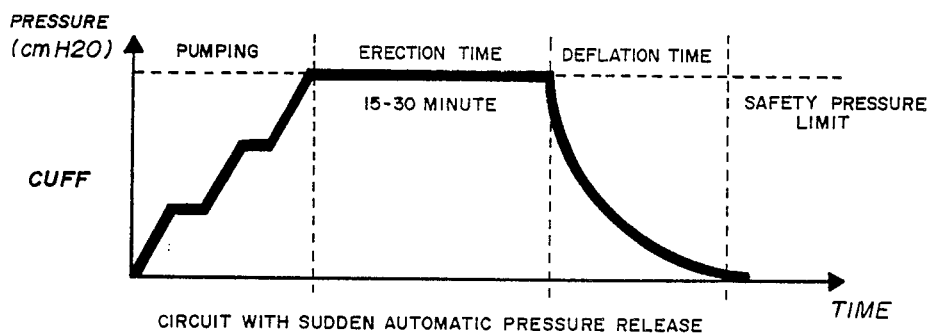
FIG. 16 graphically illustrates a complete cycle for the inflation and sudden deflation of the cuff over a relatively short time period.
Figure 17:
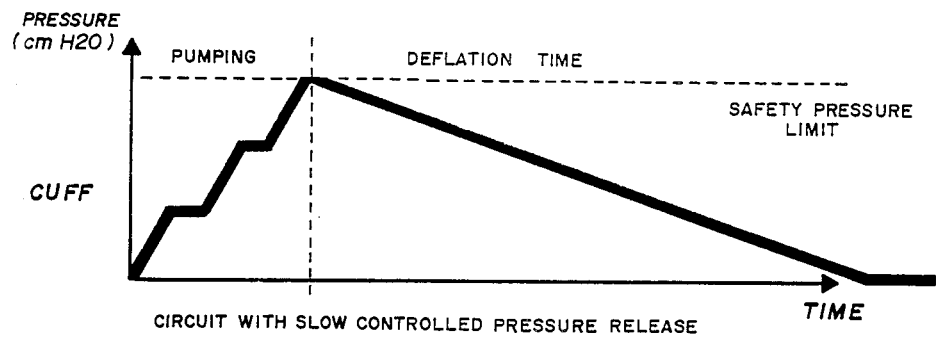
FIG. 17 is a view similar to FIG. 16, but graphically illustrates relatively slow deflation of the cuff.

FIG. 16 graphically illustrates an embodiment of system 10 wherein restrictor 28 has been calibrated and designed to provide a relatively abrupt and automatic deflation of the vesicle or vesicles employed in a particular cuff, e.g., full erection time of from 15 to 30 minutes. FIG. 17 graphically illustrates a control circuit wherein a relatively slower and gradual pressure release is automatically effected by suitable preadjustment or calibration of flow restrictor 28.

We claim:

1. A method of augmenting penile erection in a human male comprising the steps of
    identifying the corpora cavernosa, corpus spongiosum, tunica albuginea corporum cavernosorum, dorsal artery, dorsal nerve, cavernous veins, the suspensory ligament attached to the root of a penis and deep dorsal vein adjacent to the hilum and root of the penis,
    placing compression means proximal to said suspensory ligament and at least around said corpora cavernosa, cavrnous veins, and deep dorsal vein, adjacent to said hilum, outside said tunica albuginea corporum cavernosorum, and under said dorsal artery and dorsal nerve,
    selectively compressing said compression means to apply pressure against said corpora cavernosa, cavernous veins, and deep dorsal vein to restrict venous flow of blood therethrough and to augment erection of said penis for a predetermined time period, and
    removing said pressure from said corpora cavernosa and said deep dorsal vein, after said predetermined time period has elapsed, to re-establish said venous flow of blood.

2. The method of claim 1 wherein said placing step comprises placing said compression means around both said corpora cavernosa and said corpus spongiosum.

3. The method of claim 1 wherein said placing step comprises placing said compression means around said corpora cavernosa and between said corpora cavernosa and said corpus spongiosum.

4. The method of claim 1 wherein said placing step comprises surgically implanting compression means in the form of an inflatable cuff around said corpora cavernosa, cavernous veins, and deep dorsal vein and said compressing step comprises selectively inflaring and deflating said cuff.

5. The method of claim 1 further comprising surgically implanting a pump and an inflation and deflation control system in a scrotum, attaching said pump and control system to said cuff and wherein said compressing step comprises selectively squeezing said pump to inflate said cuff with a pressurized fluid.

6. The method of claim 5 further comprising automatically reducing fluid pressure in said cuff when the level of pressure of said fluid exceeds a predetermined maximum level.

7. An implantable cuff adapted to be surgically implanted around a penis of a human male comprising
    an elongated strap composed of a bio-compatible material and having a length substantially the same as the circumference of said penis,
    connector means for releasable forming said strap into an annular band adapted to be placed around said penis, and
    three longitudinally spaced vesicles formed integrally on an inner side of said strap and adapted for connection to a pump and wherein an intermediate one of said vesicles is at least generally diametrically opposed to two outer vesicles thereof when said strap is formed into said annular band.

8. The cuff of claim 7 wherein a single vesicle is integrally formed on the inner side of said strap, substantially throughout the length thereof.

9. The cuff of claim 8 wherein said vesicle defines raised end portions and an intermediate planar portion.

10. The cuff of claim 7 further comprising at least one solid elastomeric pad formed on the inner surface of said strap in longitudinally spaced relationship relative to said vesicle and wherein said vesicle and said pad are diametrically opposed to each other when said strap is formed into said annular band.

11. The cuff of claim 10 wherein said vesicle is generally planar and said pad defines a concavity therein.

12. The cuff of claim 7 wherein said strap is formed as one-piece, and said connector means attaches opposite ends of said strap together when it is formed into said annular band.

13. The cuff of claim 7 wherein said strap comprises first and second strap portions and said connector means attaches opposite ends of said strap portions together.

14. The cuff of claim 13 wherein said vesicle is formed on the inner surface of said first strap portion and an elastomeric pad is formed on the inner surface of said second strap portion, said vesicle and said pad being diametrically opposed relative to each other when said strap is formed into said annular band.

15. The cuff of claim 7 further comprising means communicating with said vesicle for selectively pressurizing and inflating a closed chamber of said vesicle with a fluid.

16. The cuff of claim 7 wherein an inner surface of said vesicle is channeled or otherwise textured.

17. An implantable cuff adapted to be surgically implanted around a penis of a human male comprising
an elongated strap composed of a bio-compatible material and having a length substantially the same as the circumference of said penis,
connector means for releasable forming said strap into an annular band adapted to be placed around said penis, and
a single vesicle formed integrally on an inner side of said strap and adapted for connection to a pump, said vesicle being formed substantially throughout the length of said strap and wherein said vesicle defines raised end portions and an intermediate planar portion.

18. An implantable cuff adapted to be surgically implanted around a penis of a human male comprising
an elongated strap composed of a bio-compatible material and having a length substantially the same as the circumference of said penis,
connector means for releasably forming said strap into an annular band adapted to be placed around said penis,
at least one inflatable vesicle formed integrally on an inner side of said strap and adapted for connection to a pump, and
at least one solid elastomeric pad formed on the inner surface of said strap in longitudinally spaced relationship relative to said vesicle and wherein said vesicle and said pad are diametrically opposed to each other when said strap is formed into said annular band, said vesicle being generally planar and said pad defining a concavity therein.

19. An implantable cuff adapted to be surgically implanted around a penis of a human male comprising
an elongated strap composed of a bio-compatible material and comprising first and second strap portions having a length substantially the same as the circumference of said penis,
connector means for releasably forming said strap into an annular band adapted to be placed around said penis and for attaching opposite ends of said strap portions together, and
at least one inflatable vesicle formed integrally on an inner side of said strap and adapted for connection to a pump.

* * * * *

UNITED STATES PATENT AND TRADEMARK OFFICE
CERTIFICATE OF CORRECTION

PATENT NO. : 4,982,731

DATED : January 8, 1991

INVENTOR(S) : Tom F. Lue, Emil E. Tanagho, Richard A, Schmidt, Curtis A. Gleason It is certified that error appears in the above-identified patent and that said Letters Patent is hereby corrected as shown below:

Column 5, line 21, delete "1;" and insert -- 11 --.

Column 6, line 33, delete "!7" and insert -- 17 --, line 61, delete "remaining" and insert -- retaining --.

IN THE CLAIMS:

Claim 1, Column 8, line 3, delete "cavrnous" and insert -- cavernous --.

Claim 4, line 28 delete "inflaring" and insert -- inflating --.

Signed and Sealed this

Twelfth Day of May, 1992

Attest:

DOUGLAS B. COMER

Attesting Officer

Acting Commissioner of Patents and Trademarks